(12) United States Patent
Dublin

(10) Patent No.: US 12,239,161 B2
(45) Date of Patent: Mar. 4, 2025

(54) SMOKING DEVICE AND METHODS OF MAKING AND USING THE SAME

(71) Applicant: Gloria O. Dublin, Efland, NC (US)

(72) Inventor: Gloria O. Dublin, Efland, NC (US)

( * ) Notice: Subject to any disclaimer, the term of this patent is extended or adjusted under 35 U.S.C. 154(b) by 521 days.

(21) Appl. No.: 17/531,283

(22) Filed: Nov. 19, 2021

(65) Prior Publication Data

US 2022/0151291 A1    May 19, 2022

Related U.S. Application Data

(60) Provisional application No. 63/115,664, filed on Nov. 19, 2020.

(51) Int. Cl.
| | |
|---|---|
| *A24F 13/08* | (2006.01) |
| *A24F 13/12* | (2006.01) |
| *A24F 19/10* | (2006.01) |
| *A61M 11/04* | (2006.01) |

(52) U.S. Cl.
CPC .............. *A24F 13/08* (2013.01); *A24F 13/12* (2013.01); *A24F 19/10* (2013.01); *A61M 11/041* (2013.01)

(58) Field of Classification Search
CPC .......... A24F 13/08; A24F 13/12; A24F 19/10; A47G 21/183; A61J 7/0038
See application file for complete search history.

(56) References Cited

U.S. PATENT DOCUMENTS 4,236,539 A * 12/1980 Mosby, Jr. et al. ...... A24D 1/12
131/175
4,410,550 A * 10/1983 Gaskill ..................... A23F 3/18
426/80

* cited by examiner

*Primary Examiner* — Christopher M Rodd
*Assistant Examiner* — Ronnie Kirby Jordan
(74) *Attorney, Agent, or Firm* — Ashley D. Johnson; Dogwood Patent and Trademark Law

(57) ABSTRACT

The presently disclosed subject matter is generally directed to a device that can be used for smoking a smokable product (such as tobacco). Particularly, the device includes a housing, cap, tube, and retainer. The housing and cap cooperate to provide a closed interior for burning an associated smokable product. The retainer functions to releasably attach the product (e.g., a cigarette) to one end of the tube. The tube passes through an opening in the cap such that a first portion of the tube is housed within the device interior and a second portion is positioned exterior to the device. The smokable product is burned within the interior of the device, and the user has access to the smoke produced by inhaling through the tube.

20 Claims, 14 Drawing Sheets

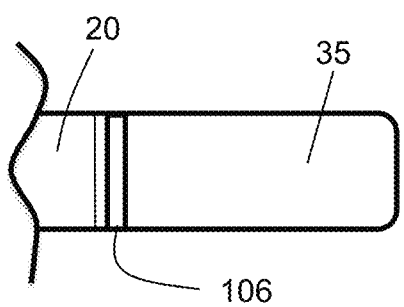
Fig. 5b
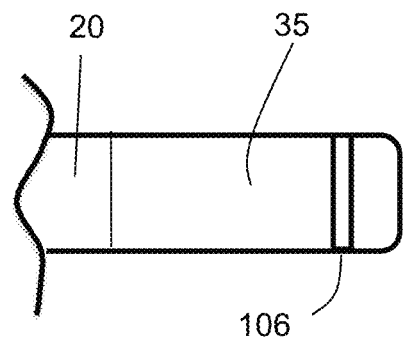
Fig. 5c
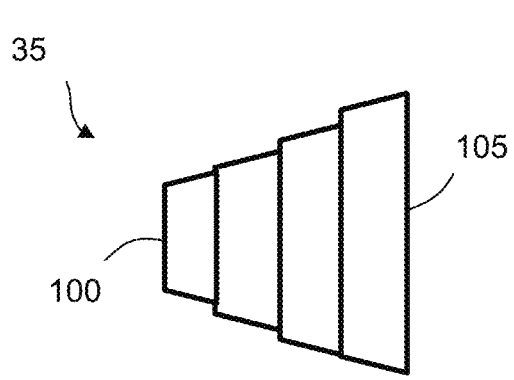
Fig. 5d
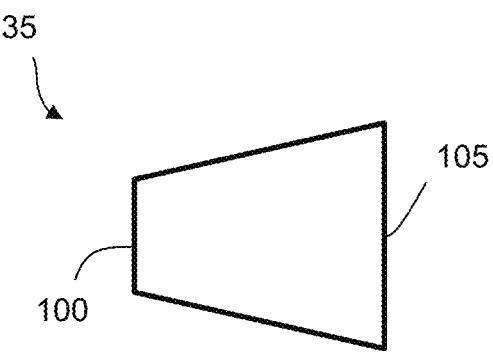
Fig. 5e
Fig. 5f
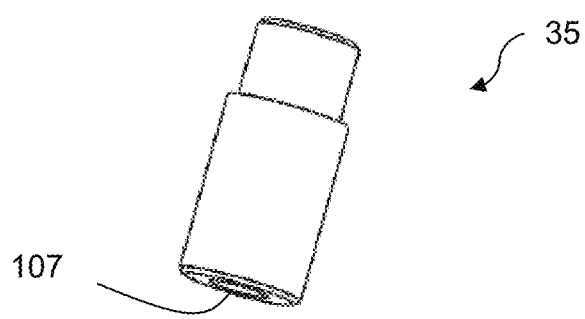

000
SMOKING DEVICE AND METHODS OF MAKING AND USING THE SAME

CROSS-REFERENCE TO RELATED APPLICATIONS

This application claims priority to U.S. Provisional Patent Application No. 63/115,664, filed Nov. 19, 2020, the entire content of which is hereby incorporated by reference.

TECHNICAL FIELD

The presently disclosed subject matter relates generally to a device that can be used to smoke tobacco and other similar products. The presently disclosed subject matter further relates to methods of making and using the device.

BACKGROUND

Smoking is the activity of burning a substance (such as tobacco) and inhaling or tasting the vapor. Tobacco includes cigarettes, cigars, and other similar substances that are burned to allow vaporization and inhalation of nicotine, tar, and other components included in tobacco leaves. In recent years, the practice of smoking has come under attack by governmental and private interest groups concerned about the potential health and environmental problems associated with smoking. Efforts by these groups have been building over the past several decades to limit and otherwise ban the practice of smoking, particularly in public places. For example, smoking is no longer allowed in most restaurants, offices, buses, airplanes, and the like. As a result, smokers must travel far distances to smoke, which can be both time consuming and inconvenient. In addition, many smokers are reluctant to smoke in public due to the stigma associated with smoking tobacco and other products. It would therefore be beneficial to provide a device that can provide smokers with the ability to smoke in a way that is predictable, convenient, and without drawing unwanted attention.

SUMMARY

In some embodiments, the presently disclosed subject matter is directed to a device for smoking a smokable product. Specifically, the device comprises a housing comprising at least one sidewall, a closed bottom end, an open top end, and an interior. The device includes a cap releasably attached to the open top end of the housing, the cap comprising a top face, a bottom face, and an opening that spans the top and bottom faces. The device further includes a tube comprising a first end, a second end, and an outer circumference that fits through the cap opening, wherein the first end of the tube is maintained outside of the housing interior, and the second end of the tube is maintained within the interior of the housing. The device comprises a tubular retainer comprising a first end and a second end, wherein the first retainer end is positioned over the second end of the tube. The second end of the retainer is removably attached to the first end and includes an opening. The interior of the retainer is configured to retain the smokeable product. The second end of the retainer includes an opening sized and shaped to retain a smokable product.

In some embodiments, the open top end includes an attachment that allows the cap to be releasably attached thereto.

In some embodiments, the attachment is selected from screw threads, magnets, fasteners, VELCRO®, buckles, snaps, clips, ties, hinges, or combinations thereof.

In some embodiments, the smokable product comprises tobacco, marijuana, herbs, or combinations thereof.

In some embodiments, the housing interior comprises a liner selected from metal, glass, ceramic material, or combinations thereof.

In some embodiments, the device further comprises a cup, ashtray, bowl, or holder positioned within the interior of the housing.

In some embodiments, the cap comprises a lip with an attachment that cooperates with the housing attachment to allow the cap to be attached and detached from the housing.

In some embodiments, the cap opening is configured as a series of slits, a hole, a cut, or combinations thereof.

In some embodiments, the cap opening is enclosed by a releasable cover.

In some embodiments, the releasable cover is attached to the cap.

In some embodiments, the retainer comprises one or more flexible materials, selected from foam, rubber, silicone, plastic, or combinations thereof.

In some embodiments, the retainer first end has a diameter that is about 0.1-10 percent larger than the diameter of the second end of the tube.

In some embodiments, the housing, cap, tube, or combinations thereof are opaque.

In some embodiments, the presently disclosed subject matter is directed to a method of smoking a product. The method comprises attaching the product to the second end of a device retainer positioned on the second end of device tube. The device comprises a housing comprising at least one sidewall, a closed bottom end, an open top end, and an interior. The device includes a cap releasably attached to the open top end of the housing, the cap comprising a top face, a bottom face, and an opening that spans the top and bottom faces. The device further includes a tube comprising a first end, a second end, and an outer circumference that fits through the cap opening, wherein the first end of the tube is maintained outside of the housing interior, and the second end of the tube is maintained within the interior of the housing. The device comprises a tubular retainer comprising a first end and a second end, wherein the first retainer end is positioned over the second end of the tube. The second end of the retainer includes an opening sized and shaped to retain a smokable product. The method includes inserting the tube through the opening in the cap, lighting the smokable product, and releasably attaching the cap to the housing. A user can inhale the smoke produced from the lit product through the first end of the tube.

BRIEF DESCRIPTION OF THE DRAWINGS

The previous summary and the following detailed descriptions are to be read in view of the drawings, which illustrate some (but not all) embodiments of the presently disclosed subject matter.

FIGS. 5b and 5c are side plan views of a device retainer configured on a tube in accordance with some embodiments of the presently disclosed subject matter.

FIGS. 5d and 5e are side plan views of a device retainer in accordance with some embodiments of the presently disclosed subject matter.

FIG. 5f is a perspective view of a retainer in accordance with some embodiments of the presently disclosed subject matter.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Figure 1A:
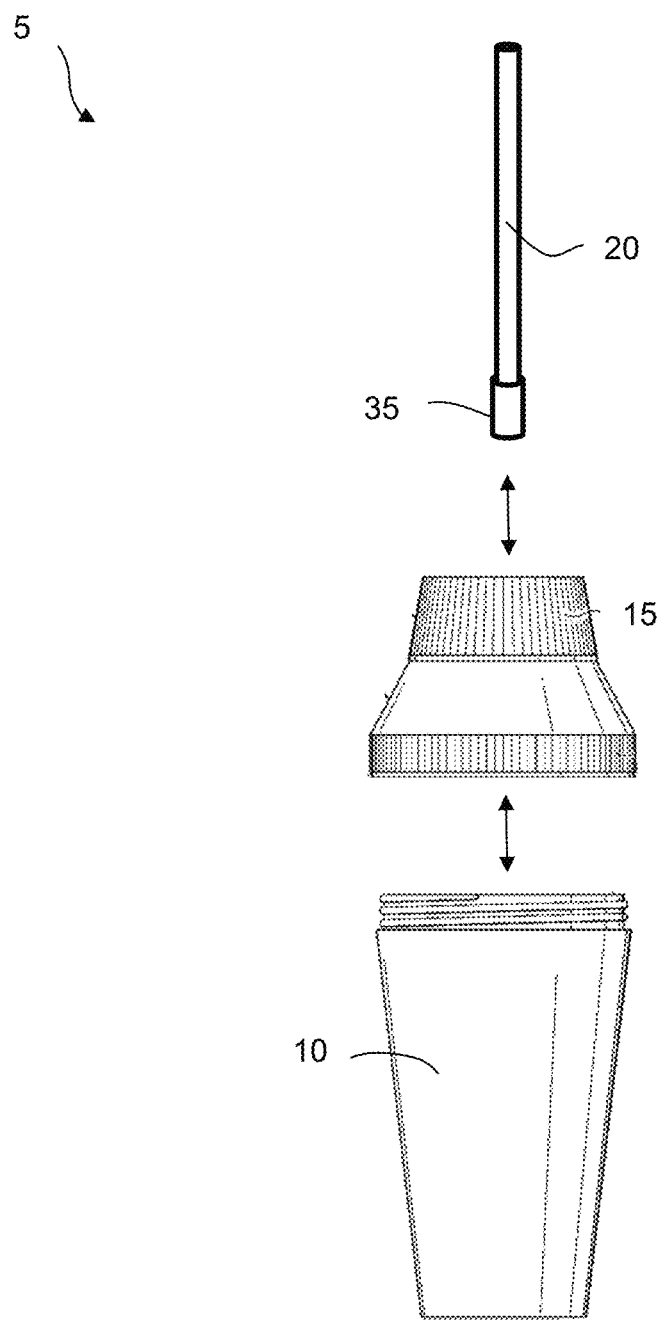
FIG. 1a is an exploded view of a device in accordance with some embodiments of the presently disclosed subject matter.
Figure 1B:
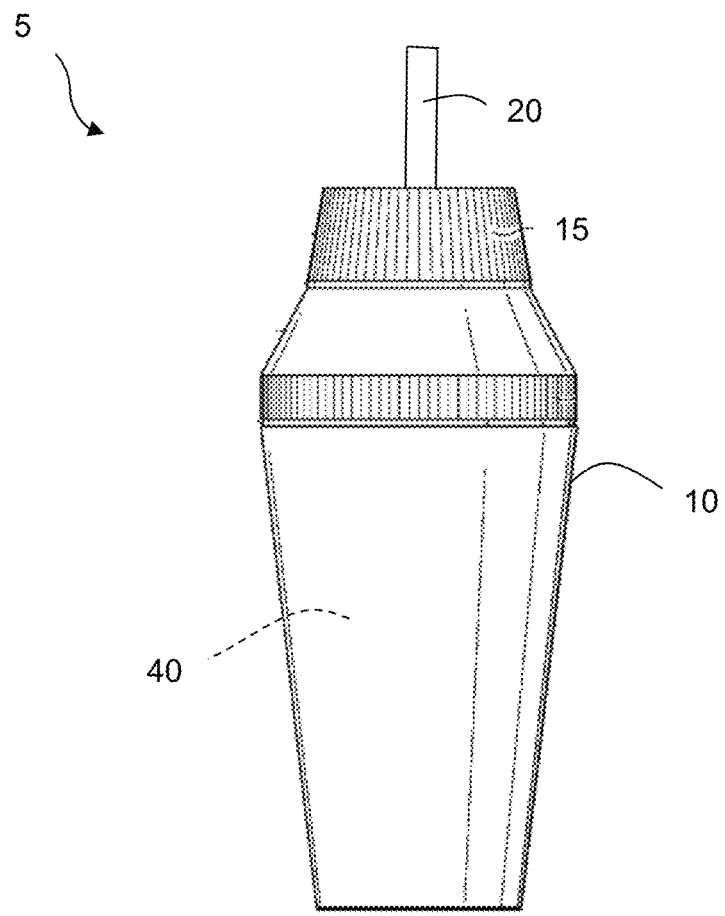
FIG. 1b is a perspective view of an assembled device in accordance with some embodiments of the presently disclosed subject matter.

The presently disclosed subject matter is generally directed to a device that can be used for smoking a product (such as tobacco). As illustrated in FIGS. 1a and 1b, device 5 includes housing 10, cap 15, tube 20, and retainer 35. The housing and cap cooperate to provide a closed interior for burning an associated smokable product. The retainer functions to releasably attach the product (e.g., a cigarette) to one end of the tube. Tube 20 passes through an opening in the cap such that a first portion of the tube is housed within the device interior and a second portion is positioned exterior to the device. The smokable product is burned within the interior of the device, and the user has access to the smoke produced via tube 20, as discussed in more detail below.

Figure 2A:
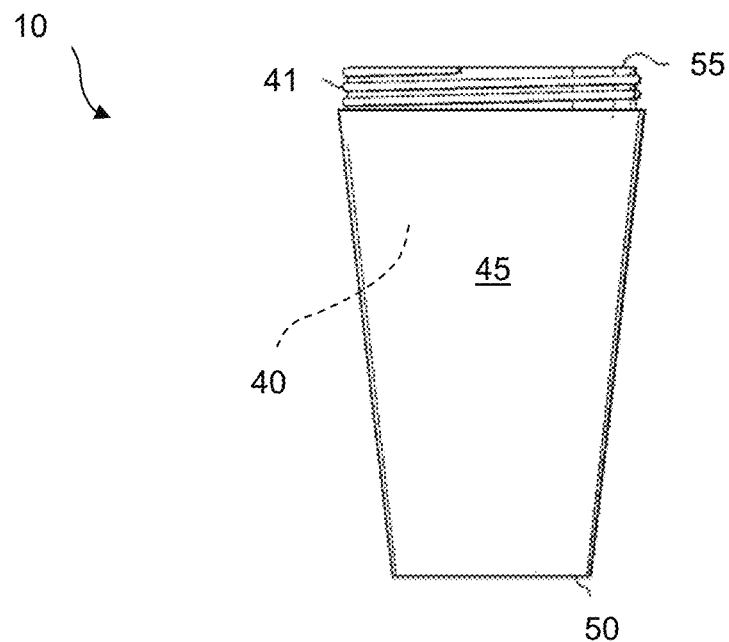
FIG. 2a is a front plan view of a device housing in accordance with some embodiments of the presently disclosed subject matter.

As set forth above, device 5 includes housing 10. The housing can include one or more sidewalls 45, closed bottom edge 50, and open top 55 that allows access to interior 40 having a predetermined volume, as illustrated in FIG. 2a. In some embodiments, the top edge of the housing can include attachment 41 that allows cap 15 to be joined and removed as desired by the user. In addition, the attachment enables an airtight seal with the cap. The attachment can include any element that allows for the releasable joining of the cap, such as (but not limited to) screw threads, magnets, fasteners, VELCRO®, buckles, snaps, clips, ties, hinges, and the like. For example, the top edge of the housing can include external screw threads that cooperate with corresponding internal screw threads positioned on the interior of the cap, allowing the cap to screw into the housing. However, it should be appreciated that any attachment mechanism can be used.

The housing includes at least one sidewall 45 that extends from open top 55 to the bottom edge of the device. The sidewalls can be angled or approximately vertical in some embodiments.

In some embodiments, housing bottom edge 50 can be approximately horizontal in the use position to allow the housing to rest easily on a flat surface (such as a table or the ground) without tipping over.

Housing 10 can have any desired cross-sectional shape. The term "cross-sectional shape" refers to the outer shape of a component when viewed on a plane transverse to the component at a right angle to the length. Thus, the housing can have a circular, oval, square, rectangular, triangular, octagonal, pentagonal, or abstract cross-sectional shape. However, the presently disclosed subject matter is not limited.

The device housing can be constructed from any desired material, such as (but not limited to) polymeric material, metal, stainless steel, ceramics, glass, or combinations thereof.

Figure 2B:
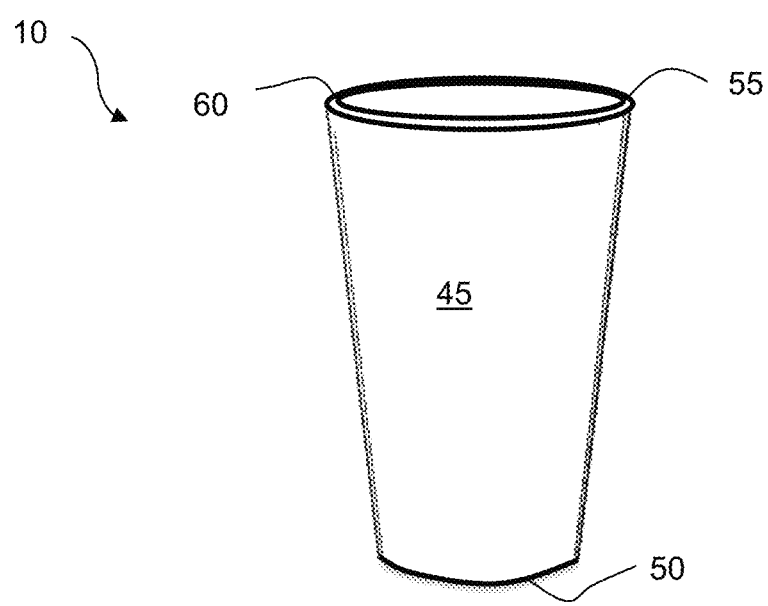
FIG. 2b is a perspective view of a device housing in accordance with some embodiments of the presently disclosed subject matter.

The interior surface of housing 10 can optionally include resilient interior lining 60, as shown in FIG. 2b. The lining can include any material that resists burning, such as metal (e.g., aluminium foil), ceramics (e.g., inorganic and non-metallic materials formed by heat treating), glass, plastic, and the like. The lining therefore protects the housing when ashes from the smokable product fall into the device interior.

Figure 2C:
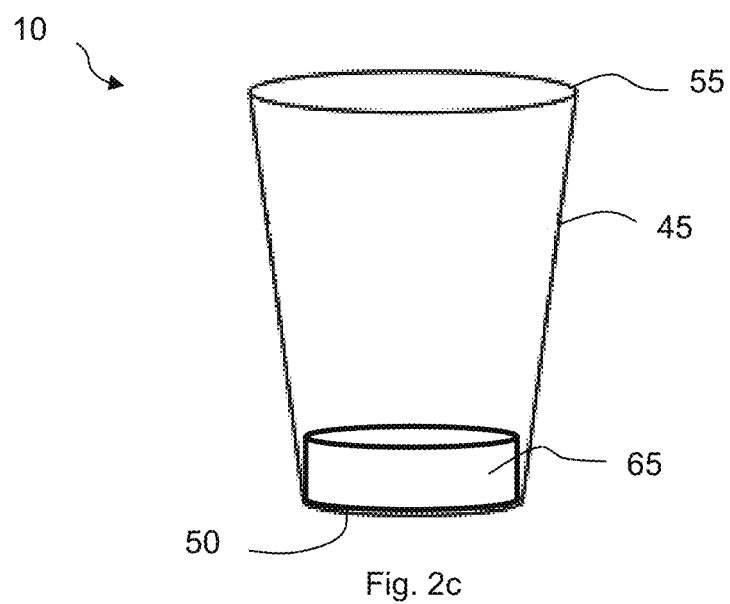
FIGS. 2c and 2d are perspective views of device housings comprising an interior container in accordance with some embodiments of the presently disclosed subject matter.
Figure 2D:
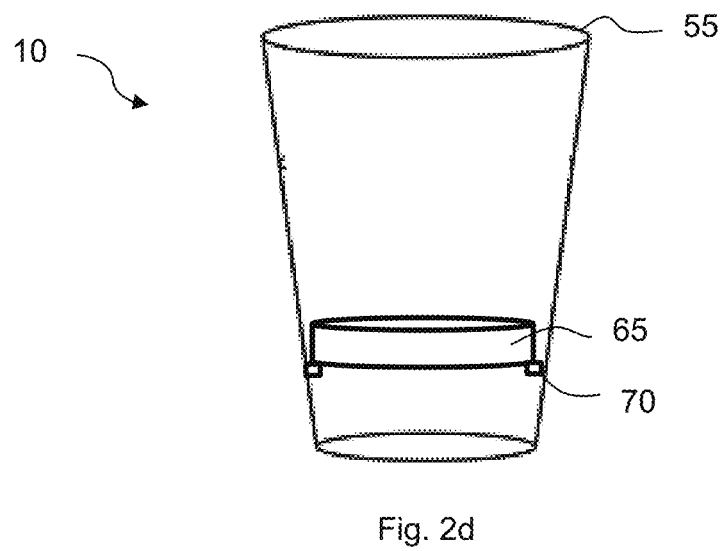

In some embodiments, housing interior 40 can include container 65 to catch ashes or other residue. The container can include any retaining element that can catch or retain ashes as they fall. The container can therefore be configured as a cup, ashtray, bowl, or other similar holder. In some embodiments, container 65 can rest on the bottom interior surface of the device as shown in FIG. 2c. Alternatively, the container interior can include one or more ledges or notches 70 that hold the container above the bottom surface of the housing, as shown in FIG. 2d. Container 65 allows ashes and residue easier to be easily removed from the interior of the device. The container can be permanently or releasably attached to housing interior 40. For example, the container can be removed and emptied in some embodiments.

Figure 2E:
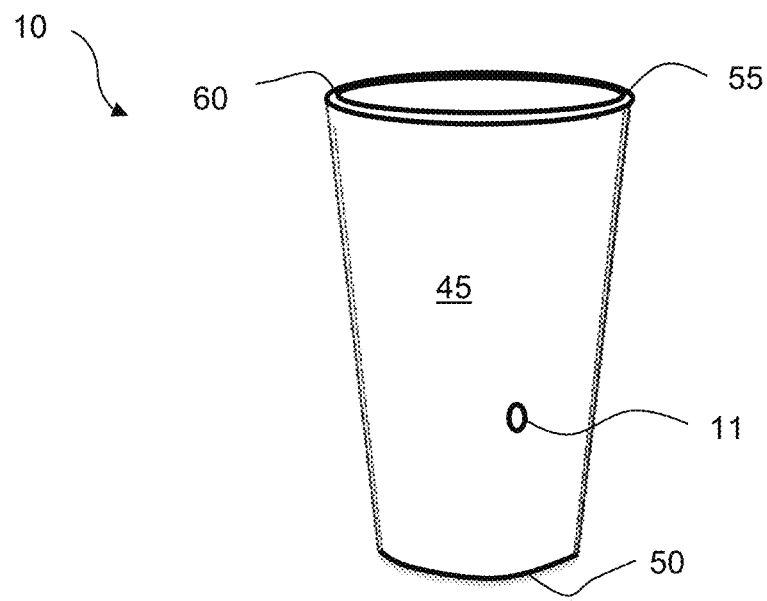
FIG. 2e is a perspective view of a device housing comprising an aperture in accordance with some embodiments of the presently disclosed subject matter.

Optionally, housing 10 can include aperture 11 configured on sidewall 45 or the bottom face, as shown in FIG. 2e. The aperture can act has a choke, allowing the user to let air in during use. Aperture 11 can be configured in any desired size and/or shape. The aperture allows a user to cover the hole with a finger while the interior of the housing fills with smoke. The user can remove their finger to expose the aperture when inhaling, thereby creating airflow that helps the user inhale. Aperture 11 can have any suitable size, such as a length and/or width of about 0.1-1 inches (e.g., at least/no more than about 0.1, 0.25, 0.5, 0.75, or 1 inch). However, the aperture can be configured with dimensions outside the stated ranges.

Figure 3A:
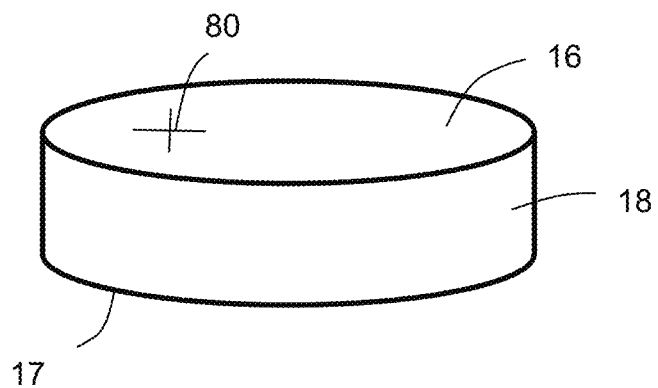
FIG. 3a is a perspective view of a device cap in accordance with some embodiments of the presently disclosed subject matter.
Figure 3B:
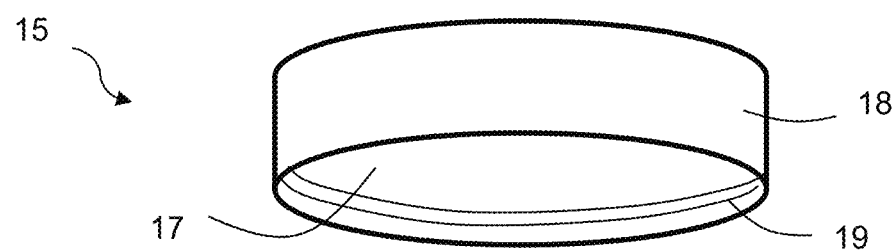
FIG. 3b is a perspective view of the underside of a device cap in accordance with some embodiments of the presently disclosed subject matter.

Device 5 further includes cap 15 that releasably attaches to the top of housing 10, creating a closed interior that will contain smoke from the smokable product when lit. FIG. 3a illustrates one embodiment of cap 15 comprising closed top edge 16 and bottom edge 17. In some embodiments, the cap includes lip 18 comprising interior screw threads 19 that cooperate with corresponding screw threads on upper edge 55 of the housing, as shown in FIG. 3b. However, any attachment mechanism can be used to attach the cap to the housing (e.g., magnets, fasteners, clips, ties, and the like).

Figure 3C:
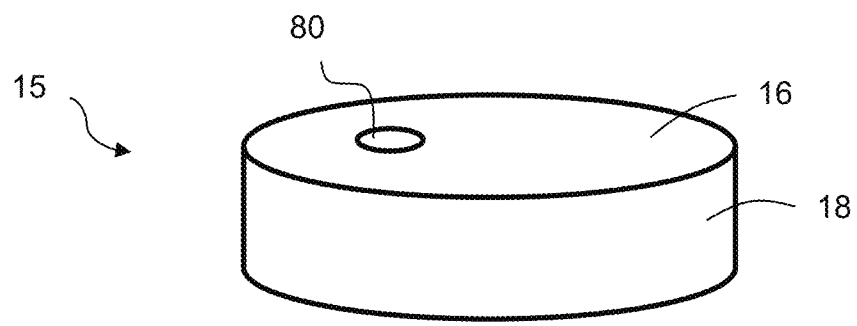
FIG. 3c is a perspective view of a device cap in accordance with some embodiments of the presently disclosed subject matter.
Figure 3D:
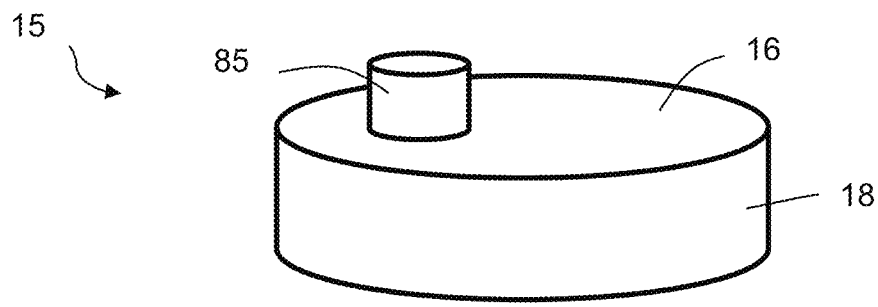
FIG. 3d is a perspective view of a device cap comprising a cap in accordance with some embodiments of the presently disclosed subject matter.
Figure 3E:
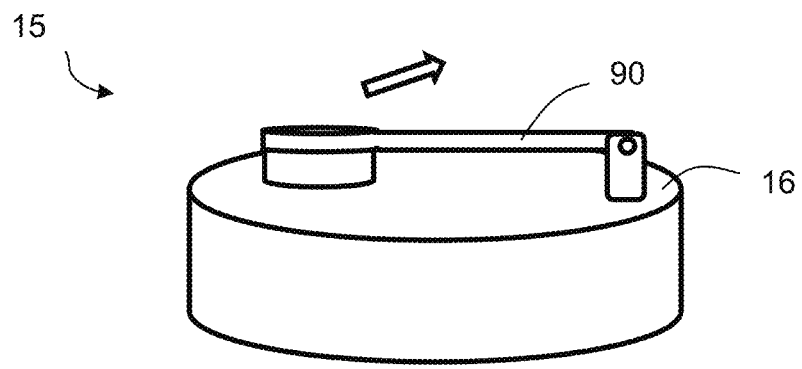
FIG. 3e is a perspective view of a device cap comprising a retainable cap in accordance with some embodiments of the presently disclosed subject matter.

Cap top surface 16 includes opening 80 sized and shaped to allow for the insertion of tube 20. In some embodiments, the cup opening can be configured as a series of slits that open in response to pressure from tube 20, as shown in FIG. 3a. Alternatively, the opening can be configured as a hole, allowing the tube to freely pass through, as illustrated in FIG. 3c. Optionally, the opening can be enclosed by cover 85 when the device is not in use, as shown in FIG. 3d. The cover can be attached over the opening by any mechanism, such as screw threads, snap-fit closure, pressure-fit closure, and the like. In some embodiments, the cover is retained on cap 15, such as with arm 90 that allows the cover to be added or removed as desired by the user. One embodiment of arm 90 is illustrated in FIG. 3e. Arm 90 can have any configuration, such as a tie, hinge, bar, spring, etc.

Figure 3F:
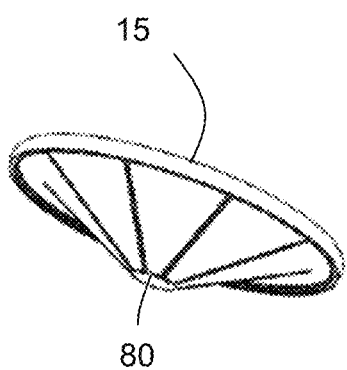
FIG. 3f is a perspective view of a device cap in accordance with some embodiments of the presently disclosed subject matter.
Figure 3G:
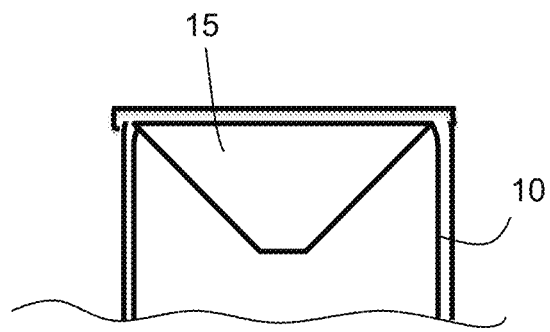
FIG. 3g is a front plan view of the device cap of FIG. 3f configured on a housing in accordance with some embodiments of the presently disclosed subject matter.

In some embodiments, the cap can include a cylindrical configuration, as shown in FIG. 3a. However, in other embodiments, the bottom surface of the cap extends in a downward direction within the interior of the housing when attached, as shown in FIGS. 3f and 3g. In these embodiments, opening 80 is configured within the lower face of the cap (and configured within the interior of the housing when attached).

Cap 15 can be constructed from any desired material (e.g., metal, wood, plastic, ceramics, rubber, elastomer, and the like). However, in some embodiments, the cap can be constructed from a flexible material, allowing the cap to be snapped or fitted onto the housing. The term "flexible" refers to the ability to bend easily and/or withstand stress tension without damage or tearing.

Figure 4A:
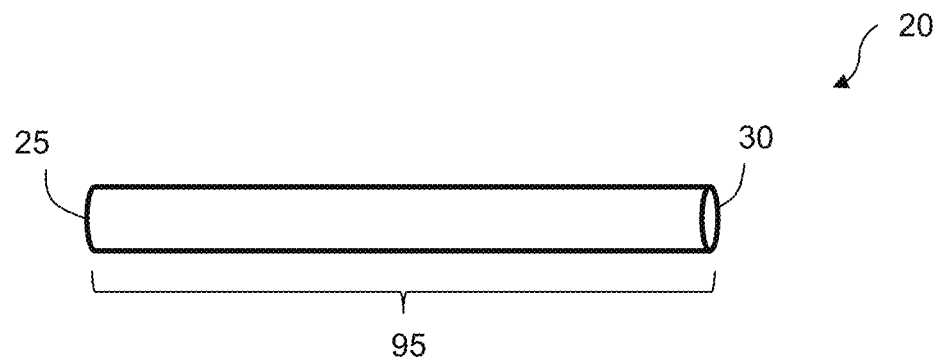
FIG. 4a is a perspective view of a device tube in accordance with some embodiments of the presently disclosed subject matter.

The disclosed device further includes tube 20, as depicted in FIG. 4a. The tube includes any hollow device to allow for the movement of fluid from first end 25 to second end 30 (or vice versa). The tube therefore acts as a conduit between the user and the interior of the device housing.

The disclosed tube can have any desired cross-sectional shape (e.g., circular, oval, square, rectangular, abstract).

Tube 20 can be any rigid, semi-rigid, or flexible member that extends through the cap to the interior of the housing. Therefore, the tube can be constructed from plastic, metal, ceramic, glass, or any combinations thereof.

Tube 20 can include any length 95 to accommodate any sized device. Thus, the tube can have a length of at least about (or no more than about) 5-30 inches.

Figure 4B:
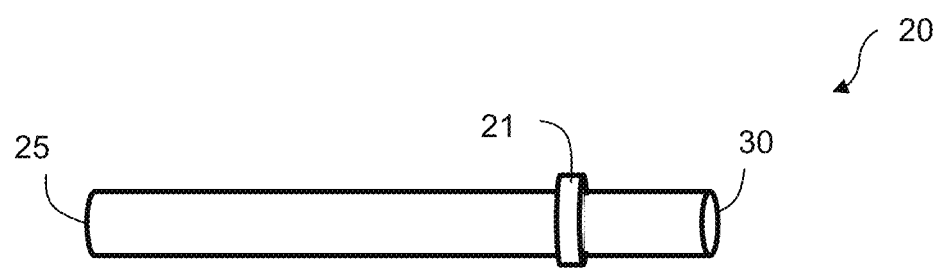
FIG. 4b is a perspective view of a device tube with an attached stop in accordance with some embodiments of the presently disclosed subject matter.

Optionally, tube 20 can include stop 21 that prevents the tube from slipping through the cap hole into the interior of the housing. Specifically, the stop fits around the circumference of the tube, as shown in FIG. 4b. The outer diameter of the stop is greater than the circumference of cap opening 80. In this way, the stop acts as a block and prevents progression of the tube into the interior of the housing.

Figure 5A:
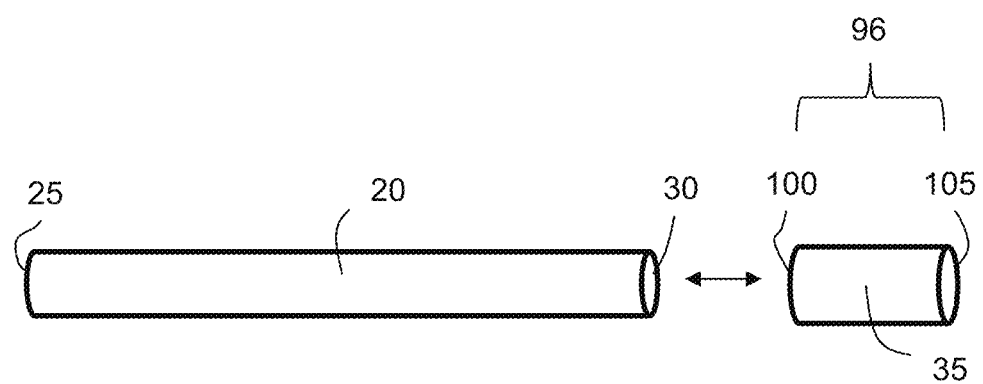
FIG. 5a is a perspective view illustrating the insertion of a device retainer on a tube in accordance with some embodiments of the presently disclosed subject matter.

As shown in FIG. 5a, second end 30 of the tube includes retainer 35. The term "retainer" refers to any element that can be used to maintain a smokable product on the second end of the tube. In some embodiments, the retainer can be constructed as a flexible tubular member comprising first end 100 and second end 105. However, the retainer can include any element, such as a clip, fastener, or other holder. The retainer is configured to hold or suspend the smokable product within the interior of the housing during burning. For example, the retainer can hold loose or pre-rolled product if desired. If loose product is used, the interior of the retainer can be configured to hold a screen 106, keeping the ashes and product from being drawn up into the tube or fall from the bottom of the retainer, as shown in FIGS. 5*b* and 5*c*. In this way, the retainer allows the product to be evenly heated which results in a greater degree of extraction.

Retainer 35 can be removably attached to the remainder of the tube, such as by screwing/unscrewing, clipping, magnets, fasteners, pressure fit closure, snap fit closure, and the like.

The retainer can have any desired configuration, such as a tubular structure with a consistent diameter along the length of the retainer, as shown in the embodiment of FIG. 5*a*. Alternatively, retainer 35 can have a ridged structure, wherein the diameter increases from first end 100 to second end 105, as illustrated in FIGS. 5*d* and 5*e*. The ridged structure can help retain cigarettes and the like of various shapes and sizes. For example, it can accommodate cigars with a relatively large diameter, as well as cigarettes with a smaller diameter.

In some embodiments, the bottom edge of the retainer includes opening 107 (e.g., a ⅜ inch diameter opening) to allow a user to light the contents of the retainer, as shown in FIG. 5*f*. The opening can also allow for the insertion of tobacco product (e.g., loose or rolled products) without separating the retainer from the remainder of the tube.

Retainer 35 can be constructed from any desired material, such as (but not limited to) rubber, silicone, plastic, and the like.

The retainer can have any desired length 96. For example, the retainer can have a length of about 0.5-5 inches (e.g., at least/no more than about 0.5, 1, 1.5, 2, 2.5, 3, 3.5, 4, 4.5, or 5 inches). However, the presently disclosed subject matter is not limited and the retainer can have a length outside the given range.

The diameter of retainer first end 100 is slightly larger than the diameter of second tube end 30. For example, the retainer diameter can be about 0.1, 1, 2, 3, 4, 5, or 10% larger than the diameter of the corresponding tube second end. In this way, the retainer can snugly fit over the second tube end and maintain the position without slipping or falling. The smokable product can then be positioned at least partially within the interior of the retainer via second end 105.

Figure 5G:
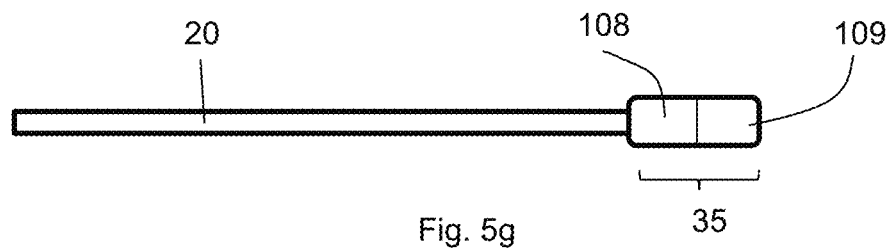
FIG. 5g is a side plan view of a device tube with a retainer in accordance with some embodiments of the presently disclosed subject matter.
Figure 5H:
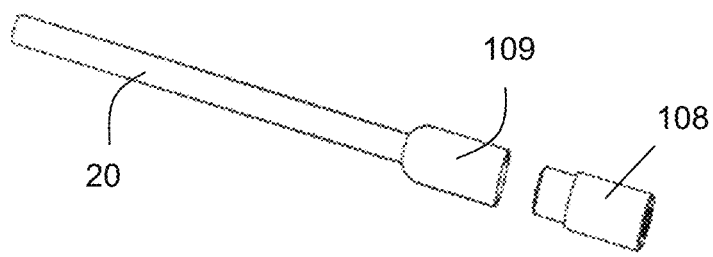
FIG. 5h is a perspective view of a device tube with a retainer in accordance with some embodiments of the presently disclosed subject matter.

In some embodiments, the retainer can include a top and bottom portion that are assembled or detached as desired by the user. As shown in FIGS. 5*g* and 5*h*, the retainer top 108 can be attached to the lower edge of the tube, forming a single piece. The retainer bottom 109 can attach or be removed from the retainer top, allowing user access to fill or clean the interior of the retainer. The retainer bottom can include opening 107 as mentioned above, allowing the user access to light the product housed within the retainer.

Figure 6A:
FIGS. 6a and 6b are side plan views of device tubing comprising an integrated retainer in accordance with some embodiments of the presently disclosed subject matter.
Figure 6B:
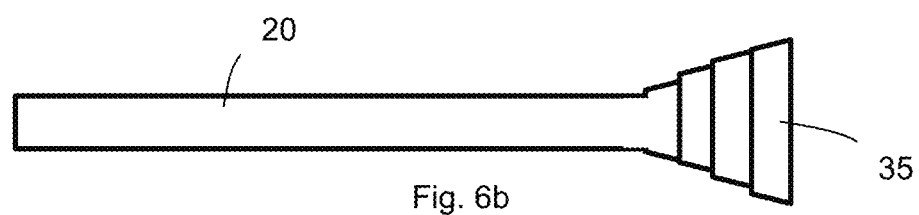

Alternatively, the tube and retainer can be configured as a single unit, as shown in FIGS. 6*a* and 6*b*. As shown, the tube can include a retainer configured at second end 30. In this way, the retainer is remains at the tube second end and cannot be removed or dropped into the interior of the housing.

Device 5 can have any desired size and volume, such as about 10-50 ounces.

The housing, cap, tube, retainer, or any combination thereof, can have slip-proof grips to enable the consumer to grip each piece securely while assembling or disassembling the device components back together. For example, the slip-proof grip can include a ridged or grooved surface of the housing. Alternatively, the grip can include a higher coefficient of friction compared to the remainder of the housing material.

It should be appreciated that device 5 can have any desired shape and/or structure and is not limited to the configurations shown in the Figures. For example, the housing can have a cylindrical shape, conical shape, domed shape, and/or a tapered construction. The device can further be configured in a decorative shape, such as holiday images, animals, faces, flowers, or abstract shapes. One or more components of the device can further include any outer adornments, such as glitter, crystals, and the like.

In some embodiments, one or more device components (e.g., housing 10, cap 15, tube 20) can include materials that are opaque or non-light transmitting. In this way, third parties cannot view the contents contained within housing 10. In addition, when the smokable product is stored within the device, it is free from exposure to light which reduces the degradative effect that can arise.

Figure 7A:
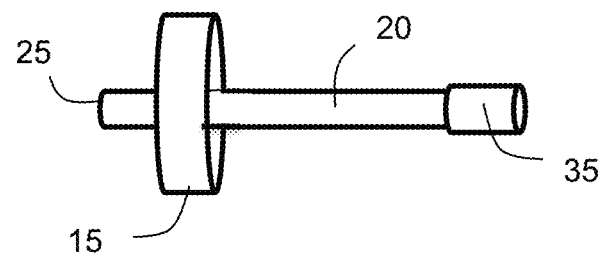
FIG. 7a is a perspective view of a cap comprising a tube and retainer in accordance with some embodiments of the presently disclosed subject matter.
Figure 7B:
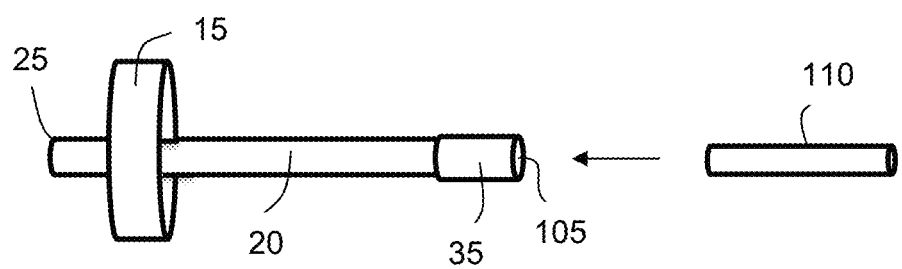
FIGS. 7b and 7c are perspective views illustrating a smokable product inserted into the device retainer in accordance with some embodiments of the presently disclosed subject matter.
Figure 7C:
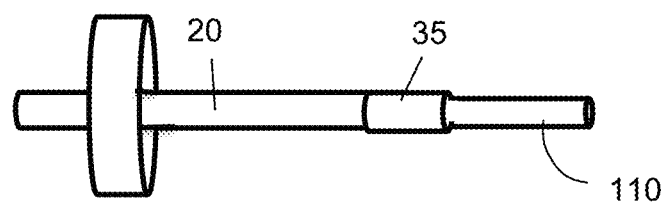

In use, the device can be assembled such that tube 20 extends through cap opening 80. The cap is then removed from the housing, as shown in FIG. 7*a*. For example, the housing threads can be unattached from the cap threads by an unscrewing action. The retainer is then attached to tube second end 30. Smokable product 110 can then be positioned within second end 105 of the retainer, as shown in FIGS. 7*b* and 7*c*.

The term "smokable product" refers to any product that can be smoked, such as (but not limited to) those derived from a plant and used for medicinal, therapeutic, recreational, aromatic, or culinary purposes.

Thus, the smokable product can comprise cannabis (herbal marijuana). The vapor produced from cannabis when burned has long been found to provide medicinal benefits, such as in treating cancer, glaucoma, seizures, multiple sclerosis, epilepsy, cancer, HIV, amongst other ailments. A person receiving treatment from cannabis may experience a stimulation in appetite, pain relief, relaxation, reduced inflammation and/or other benefits. These effects are due, in large part, to cannabinoids, which are chemical compounds found in cannabis, that act on the cannabinoid receptor system of the brain. In certain regions within the United States, physicians are able to prescribe the use of cannabis for patients.

In other embodiments, smokable product 110 can comprise tobacco, such as conventional cigarettes and cigars.

In still other embodiments, the smokable product can include herbs, such as cloves and the like.

Figure 7D:
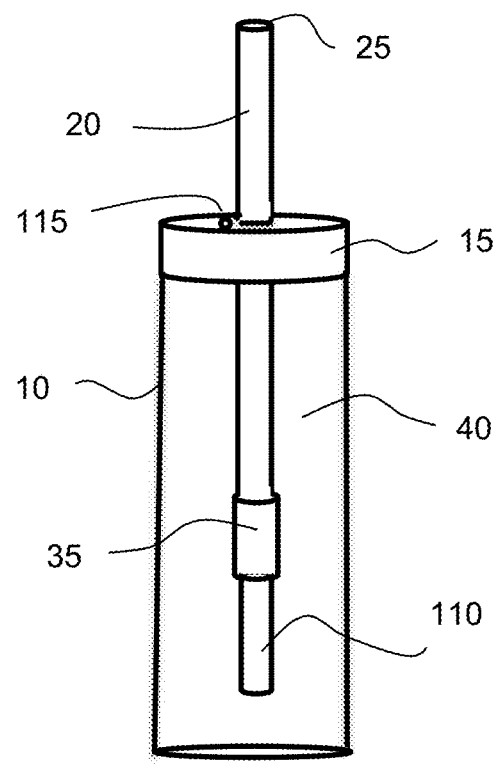
FIG. 7d is a front plan view illustrating a device in accordance with some embodiments of the presently disclosed subject matter.

Smokable product 110 is therefore maintained within the open end of the retainer. The product can then be lit using conventional methods (a lighter, matches, etc.). The cap with the attached tube, retainer, and tobacco product is then reattached to housing 10, as shown in FIG. 7*d*. In this way, the lit product is maintained within interior 40 of the housing. Because the housing with the cap attached is a closed device, the interior of the housing fills with smoke from product 110. The user can then inhale from first tube end 25 to consume the smoke.

In some embodiments, a pressure-equalizing bore hole can compensate for the vacuum pressure created by the user sucking on tube 20. Bore hole 115 can be positioned on any surface of the device, such as on the top surface of cap 15. It should be appreciated that the bore hole is optional.

Ashes and other residue from the lit tobacco product can fall within the interior of the housing. Because the housing interior is constructed from inert materials, there is no risk of fire. In some embodiments, the tobacco ash and residue are maintained in container 65 within the housing interior.

Once the tobacco product has been used, the user can remove (e.g., unscrew) the cap from the cap and replace the used tobacco product and repeat the process.

Figure 8:
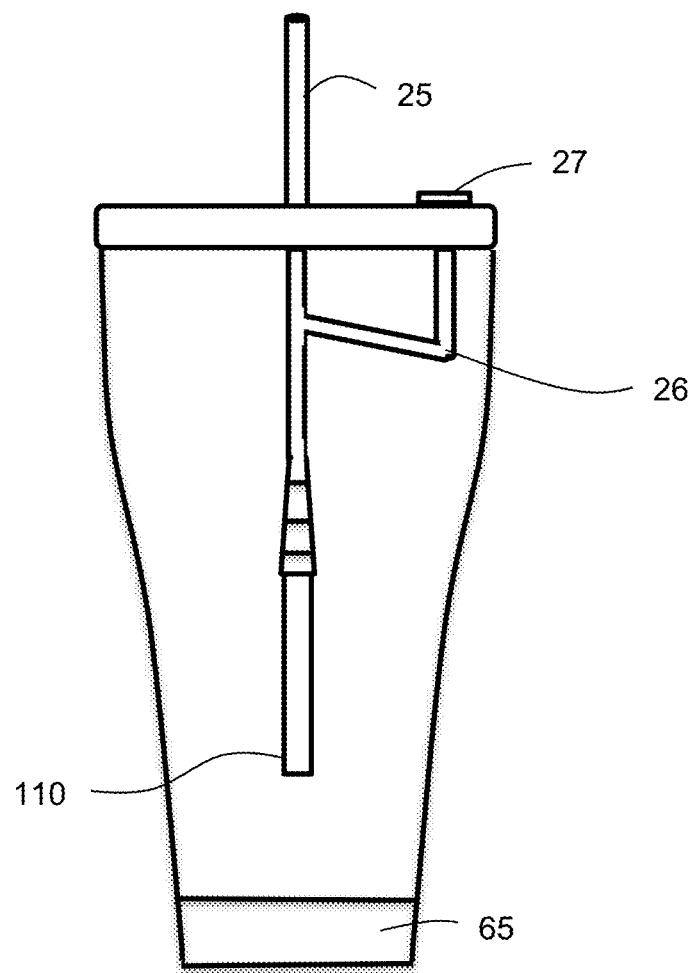
FIG. 8 is an alternate embodiment of a device in accordance with some embodiments of the presently disclosed subject matter.

FIG. 8 illustrates an alternate embodiment of device 5. As shown, tube 25 can include leg 26 that diverts outward and upward to connect with choke 27 in cap 15. The leg can be configured at any desired angle or shape so long as it connects the tube main body with the choke. The term "choke" refers to any type of valve that can release or control the smoke produced in the housing. For example, the choke can be opened to vent off excess smoke. Alternatively, the choke can be closed to retain the smoke within the interior of the housing.

Figure 9:
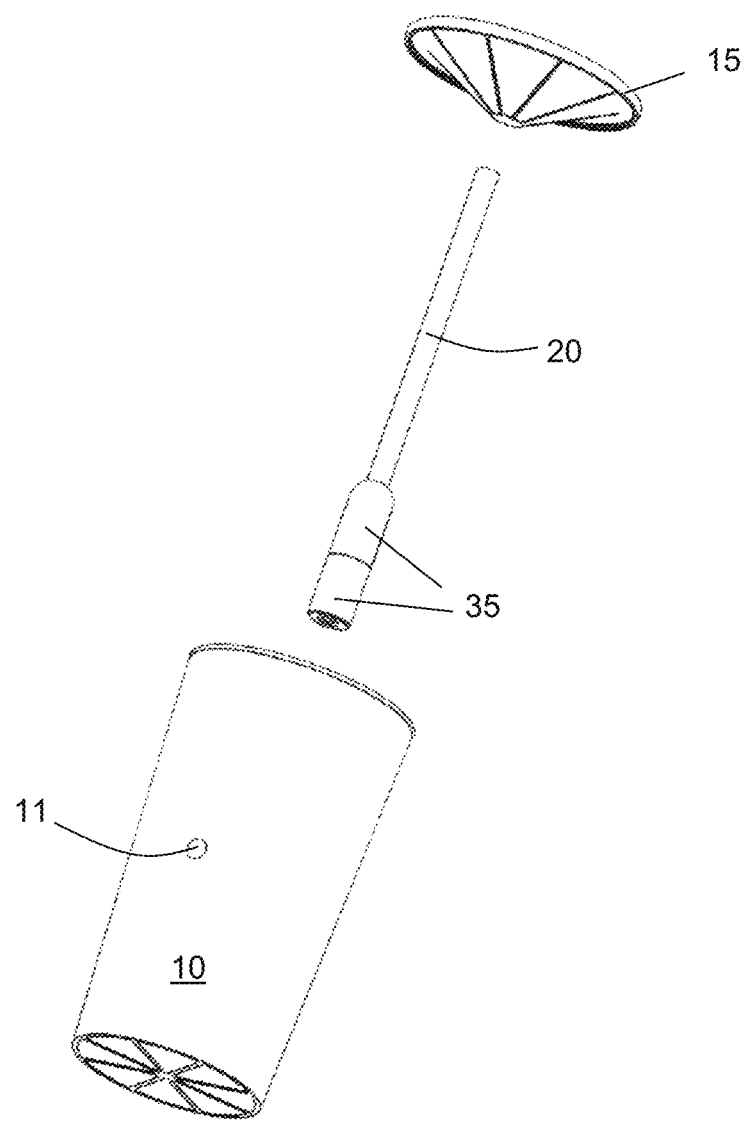
FIG. 9 is an alternate embodiment of a device in accordance with some embodiments of the presently disclosed subject matter.

FIG. 9 illustrates an additional embodiment of device 5 comprising two piece retainer 35 that attaches to tube 20. The device can also include optional aperture 11 that acts as a choke.

The interior of the housing can be cleaned when needed (e.g., when excessive ash or other residue accumulates). Any method can be used to clean the device, such as the use of soap and water.

Advantageously, the user can smoke in public without drawing attention to the practice. Particularly, it appears to the general public that the user is taking a drink of a beverage when in actuality the user is smoking product 110.

The disclosed device offers many benefits to the user. For example, the disclosed device can be used in any setting where the consumer desires to have a convenient smoking experience.

The disclosed device enables an enjoyable consumer experience by providing a unique, convenient, and fun approach to consuming tobacco and other smokable products.

Device 5 is convenient and easy to use by a variety of individuals.

The device is also easily cleaned and can be reused any number of times.

Further, device 5 is portable, allowing a user to conveniently carry it when traveling, on the go, or even around the house.

The disclosed device is cost effective to manufacture because it is made from conventional materials.

While the presently disclosed subject matter has been particularly shown and described with references to preferred embodiments thereof, it will be understood by those skilled in the art that various changes in form and details may be made herein without departing from the spirit and scope of the invention as defined by the appended claims.

What is claimed is:

1. A device for smoking a smokable product, the device comprising:
   a housing comprising at least one sidewall, a closed bottom end, an open top end, and an interior;
   a cap releasably attached to the open top end of the housing, the cap comprising a top face, a bottom face, and an opening that spans the top and bottom faces;
   a tube comprising a first end, a second end, and an outer circumference that fits through the cap opening, wherein the first end of the tube is maintained outside of the housing interior, and the second end of the tube is maintained within the interior of the housing;
   a retainer comprising a first end and a second end, wherein the first retainer end is positioned over the second end of the tube;
   wherein the second end of the retainer is removably attached to the first end and includes an opening;
   wherein the interior of the retainer is configured to retain the smokable product.

2. The device of claim 1, wherein the open top end includes an attachment that allows the cap to be releasably attached thereto.

3. The device of claim 2, wherein the attachment is selected from screw threads, magnets, fasteners, hook and loop fasteners, buckles, snaps, clips, ties, hinges, or combinations thereof.

4. The device of claim 1, wherein the smokable product comprises tobacco, marijuana, herbs, or combinations thereof.

5. The device of claim 1, wherein the housing interior comprises a liner selected from metal, glass, ceramic material, or combinations thereof.

6. The device of claim 1, further comprising a cup, ashtray, bowl, or holder positioned within the interior of the housing.

7. The device of claim 2, wherein the housing sidewall includes an opening.

8. The device of claim 1, wherein the cap includes one face that extends into the interior of the housing when attached to the housing.

9. The device of claim 1, wherein the cap opening is enclosed by a releasable cover.

10. The device of claim 9, wherein the releasable cover is attached to the cap.

11. The device of claim 1, wherein the retainer comprises one or more flexible materials, selected from foam, rubber, silicone, plastic, or combinations thereof.

12. The device of claim 1, wherein the retainer first end has a diameter that is about 0.1-10 percent larger than the diameter of the second end of the tube.

13. The device of claim 1, wherein the housing, cap, tube, or combinations thereof are opaque.

14. A method of smoking a product, the method comprising:
   attaching the product to the second end of a device retainer positioned on the second end of device tube, wherein the device comprises:
      a housing comprising at least one sidewall, a closed bottom end, an open top end, and an interior;
      a cap releasably attached to the open top end of the housing, the cap comprising a top face, a bottom face, and an opening that spans the top and bottom faces;
      a tube comprising a first end, a second end, and an outer circumference that fits through the cap opening, wherein the first end of the tube is maintained outside of the housing interior, and the second end of the tube is maintained within the interior of the housing;
      a tubular retainer comprising a first end and a second end, wherein the first retainer end is positioned over the second end of the tube;
      wherein the second end of the retainer is removably attached to the first end and includes an opening;
      wherein the interior of the retainer is configured to retain the smokable product;
   inserting the tube through the opening in the cap;
   lighting the smokable product;
   releasably attaching the cap to the housing;
   wherein a user can inhale the smoke produced from the lit product through the first end of the tube.

15. The method of claim 14, wherein the product comprises tobacco, marijuana, herbs, or combinations thereof.

16. The method of claim 14, wherein the housing interior comprises a liner selected from metal, glass, ceramic material, or combinations thereof.

17. The method of claim 14, further comprising a cup, ashtray, bowl, or holder positioned within the interior of the housing.

18. The method of claim 14, wherein the retainer comprises one or more flexible materials, selected from foam, rubber, silicone, plastic, or combinations thereof.

19. The method of claim 14, wherein the retainer first end has a diameter that is about 0.1-10 percent larger than the diameter of the second end of the tube.

20. The method of claim 14, wherein the housing, cap, tube, or combinations thereof are opaque.

\* \* \* \* \*